United States Patent [19]
Florin-Robertsson et al.

[11] Patent Number: 5,734,026
[45] Date of Patent: Mar. 31, 1998

[54] PROCESS FOR MANUFACTURING CRYSTALS OF GROWTH HORMONE AND CRYSTALS THEREBY OBTAINED

[75] Inventors: Ebba Florin-Robertsson, Stockholm; Elvy Hökby, Enskede; Ronny Lundin, Ekerö; Sirkka Thomé, Stockholm; Gertrud Westin-Sjödahl, Södertälje, all of Sweden

[73] Assignee: Pharmacia & Upjohn Aktiebolag, Stockholm, Sweden

[21] Appl. No.: 424,450

[22] PCT Filed: Oct. 27, 1993

[86] PCT No.: PCT/SE93/00885

§ 371 Date: May 24, 1995

§ 102(e) Date: May 24, 1995

[87] PCT Pub. No.: WO94/10192

PCT Pub. Date: May 11, 1994

[30] Foreign Application Priority Data

Oct. 28, 1992 [SE] Sweden ................................ 9203175
Jul. 2, 1993 [SE] Sweden ................................ 9302278
Oct. 27, 1993 [SE] Sweden ................................ SE93/00885

[51] Int. Cl.$^6$ ............................ C07K 14/61; C07K 1/14; C07K 1/30
[52] U.S. Cl. ................ 530/424; 530/399; 530/418; 530/419; 530/422
[58] Field of Search ................ 530/350, 399, 530/418, 419, 422, 424; 514/2; 117/43; 554/211

[56] References Cited
FOREIGN PATENT DOCUMENTS

WO 91/18927 12/1991 WIPO.
WO 91/19742 12/1991 WIPO.
WO 92/01463 2/1992 WIPO.
WO 92/00998 12/1992 WIPO.
WO 94/10192 5/1994 WIPO.

OTHER PUBLICATIONS

Crystallization and X-ray Data Collection on Human Growth Hormone, J. Mol. Biol. (1989) vol. 208, pp. 719–721.

Jones et al., Crystallization of Authentic Recombinant Human Growth Hormone, Bio/Technology, vol. 5 (1987), pp. 499–500.

Jones et al., Crystallization of Authentic Recombinant Human Growth Hormone, Chemical Abstracts, vol. 107 (1987), Item 109575.

McPherson "Preparation and Analysis of Protein Crystals" John Wiley and Sons, pp. 102–104, 1982.

Ollis et al "Protein Crystallization" Academic Press pp. 646–659, 1990.

*Primary Examiner*—John Ulm
*Assistant Examiner*—Christine Saoud
*Attorney, Agent, or Firm*—Pollock, Vande Sande & Priddy

[57] ABSTRACT

A process for manufacturing crystals of growth hormone (GH) comprising the steps of:

i) mixing GH with an aqueous solution comprising a buffer and a chemical compound with the general formula (1):

$$Ar\text{—}[\text{—}CR_1R_2\text{—}]n\text{—}[\text{—}C R_3R_4\text{—}]m\text{—}C R_5R_6\text{—}OH \quad (1)$$

in which Ar is phenyl, alkyl-substituted phenyl, naphthyl, or alkyl-substituted naphthyl, $R_1$ to $R_6$ is H, OH or alkyl and n and m is 0 or 1;

ii) incubating; and iii) isolating the crystals is provided. The crystals are in the form of needles, trigonal forms, cubes or parallel-epipeds with a length of at least 20 microns.

24 Claims, 1 Drawing Sheet

PROCESS FOR MANUFACTURING CRYSTALS OF GROWTH HORMONE AND CRYSTALS THEREBY OBTAINED

The present invention relates to a process for manufacturing crystals of growth hormone (GH) or functional derivatives thereof. It also relates to crystals of growth hormone and compositions containing them.

Growth hormone can be both human and animal such as human growth hormone (hGH), bovine growth hormone (bGH), fish and porcine growth hormone (pGH).

hGH is a protein consisting of a single chain of 191 amino acids. The molecule is cross-linked by two disulphide bridges and the monomeric form has a molecular weight of 22 kDa. However, pituitary human growth hormone is not homogeneous. For example, a smaller 20 kDa hGH variant produced from the same gene is also known. The "basic hGH" variant (hGH-V) expressed by the placenta during pregnancy is another analogue which is a product of a separate gene. Like the 22 kDa hGH it consists of 191 amino acids but in various positions throughout the molecule 13 of them are different. See e.g. Bewley T. A. et al; Adv Enzymol; 42; 73–166; 1975 and Frankenne F. et al; J Clin. Endocrin and Metabol; 66; 1171–80; 1988.

Recombinant hGH (22 kDa) has been commercially available for several years. It is preferred over the pituitary derived products because the product prepared from human tissue might contain infectious agents such as that for the Creutzfeldt-Jacob's disease. Two types of therapeutically useful recombinant hGH preparations are present on the market: the authentic one, e.g. Genotropin®, Kabi Pharmacia AB, and an analogue with an additional methionine residue at the N-terminal end, e.g. Somatonorm®.

hGH is used to stimulate linear growth in patients with hypopituitary dwarfism or Turner's syndrome but other indications have also been suggested.

The stability of proteins is generally a problem in the pharmaceutical industry.

It has often been solved by drying the protein in different drying processes, such as freeze-drying. The protein has thereafter been distributed and stored in dried form. The patient necessarily has to reconstitute the dried protein in a solvent before use, which is a disadvantage and of course is an inconvenience for the patient.

The freeze-drying process is a costly and time consuming process step, and it would be of great advantage if this step could be avoided, when preparing a commercial product of a protein.

For a patient, who needs daily injections of a growth hormone e.g. hGH, and especially when the patient is a child, it is of importance that the product is easy to handle, to dose and inject. The reconstitution of freeze-dried hGH demands prudence and carefulness and should preferably be avoided, but is the only method available today.

Different solutions to this problem have been disclosed, but until now no product has appeared on the market.

In WO 89/09614 to Genentech, a stabilized formulation of hGH comprising glycine, mannitol and a buffer is disclosed and in a preferred embodiment a non-ionic surfactant such as polysorbate 80 is added. Sodium-phosphate is suggested as buffer substance. The formulation has an increased stability in a lyophilized formulation and upon reconstitution.

Another possibility of administering growth hormone in a solution is to add a block copolymer containing polyoxyethylene-polyoxypropylene according to EP 211 601 to International Minerals and Chemical Corporation.

This solution provides for a prolonged release upon administration to the animal.

A different way to circumvent the stability and production problems of GH is presented in this patent application.

By crystallization a new way of manufacturing growth hormone can be achieved.

Crystals of growth hormone can also be used for various new formulations of the hormone like e.g. injectable suspensions, implants and topical formulations of various types.

Crystallization of growth hormone has not previous been possible to perform in an industrial way.

Clarkson et al reports in J Mol Biol (1989), 208, 719–721 of three distinct crystallization methods, different from the earlier described method.

The following methods were used:
1. Hanging drop and using ethanol or methanol in the buffer in which tetragonal bipyramids were obtained with a size of $10^{-3}$ mm$^3$, and a cell dimension of 134 Å (0, 0134 micron) after up to a year.
2. Hanging drop, using acetone in the buffer in which trigonal prisms were obtained with a size of $2\times10^{-3}$ mm$^3$ after 3 to 14 days.
3. Batchwise using paraldehyde and obtaining orthorhombic parallelepipeds with a size of $2\times10^{-3}$ mm$^3$ after several weeks.

The authors commented that they did not succeed in obtaining large single crystals.

In WO 92/00998, Novo Nordiska NS, a method of producing chemically stable and biological active growth hormone cation crystals are disclosed. The method comprises the steps: addition of cations to a solution of GH at a pH between 5 and 8, growing of crystals at a temperature of 0°–30° C. and isolation of the crystal. The crystal obtained is a cation GH crystal.

The preferred cation is $Zn^{2+}$ and preferably an organic solvent is added together with the cation.

The obtained crystals always include a cation and are small. In the examples the length of the zinc containing crystals varies between 3 and 12 micron.

In an article by B. C. Cunningham et al. in Science, Volume 253, pp. 545–548, 1991, dimerization of hGH by zinc is disclosed. There is a demand on the market for better ways of administering hGH. Some ways to meet this demand is to provide either ready to use injection solutions or to provide an injectable depot formulation, e.g., as suspended crystals of hGH. Crystals of hGH can be used in a suspension or in an aqueous injectable solution together with buffers and with or without preservatives. They can also be used in depot formulation, as e.g. an oily or aqueous suspension or as an implant, and thus give a slow release of the medicament. If the crystals are large enough, the can be used as powder and be spread on the surface, e.g., on a wound. Very small particles are not suitable as they form dust and cannot be used for direct use.

SUMMARY OF INVENTION

We have to our great surprise found a new method for producing pure, active GH crystals without the addition of cations or solvents such as methanol, ethanol, acetone or paraldehyde, which are not acceptable from a therapeutic viewpoint.

By this new method the crystals could be formed within a very short period of time. When using some of the named compounds, see example 22, the crystals were formed instantly and for some others within one hour. This can be compared with the method presented by Carlsson et al. which only produces crystals after several weeks. By the addition of a chemical compound with the general structure (I) to an aqueous solution of GH, crystals of GH can be easily and rapidly formed. The addition can preferably be performed in the last purification step by dialysis or chromatography with the solution containing the compound.

With this method it is possible to vary the size of the crystals depending on the conditions and time, which is a great advantage when preparing different formulations for administration of hGH.

The obtained GH in crystals is a material normally containing over 80% monomeric GH.

It could be a great advantage in the manufacturing of hGH, that there is a quick method for preparing crystals and with avoidance of cations.

This method can also be used in the technical process for purification and manufacturing.

The new process for manufacturing crystals of growth hormone (GH) or functional derivatives thereof thus includes the steps:

i) mixing GH or functional derivatives thereof with an aqueous solution comprising a buffer and a chemical compound with the general formula (I):

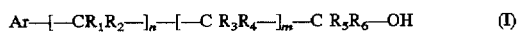

in which

Ar is phenyl, alkyl-substituted phenyl, naphthyl, or alkyl-substituted naphthyl $R_1$ to $R_6$ is H, OH or alkyl n and m is 0 or 1 ii) incubation iii) isolating the crystals by known methods.

BRIEF DESCRIPTION OF DRAWING

The FIGURE is a microscopy of formed crystals.

BEST AND VARIOUS MODES FOR CARRYING OUT INVENTION

Figure 1:
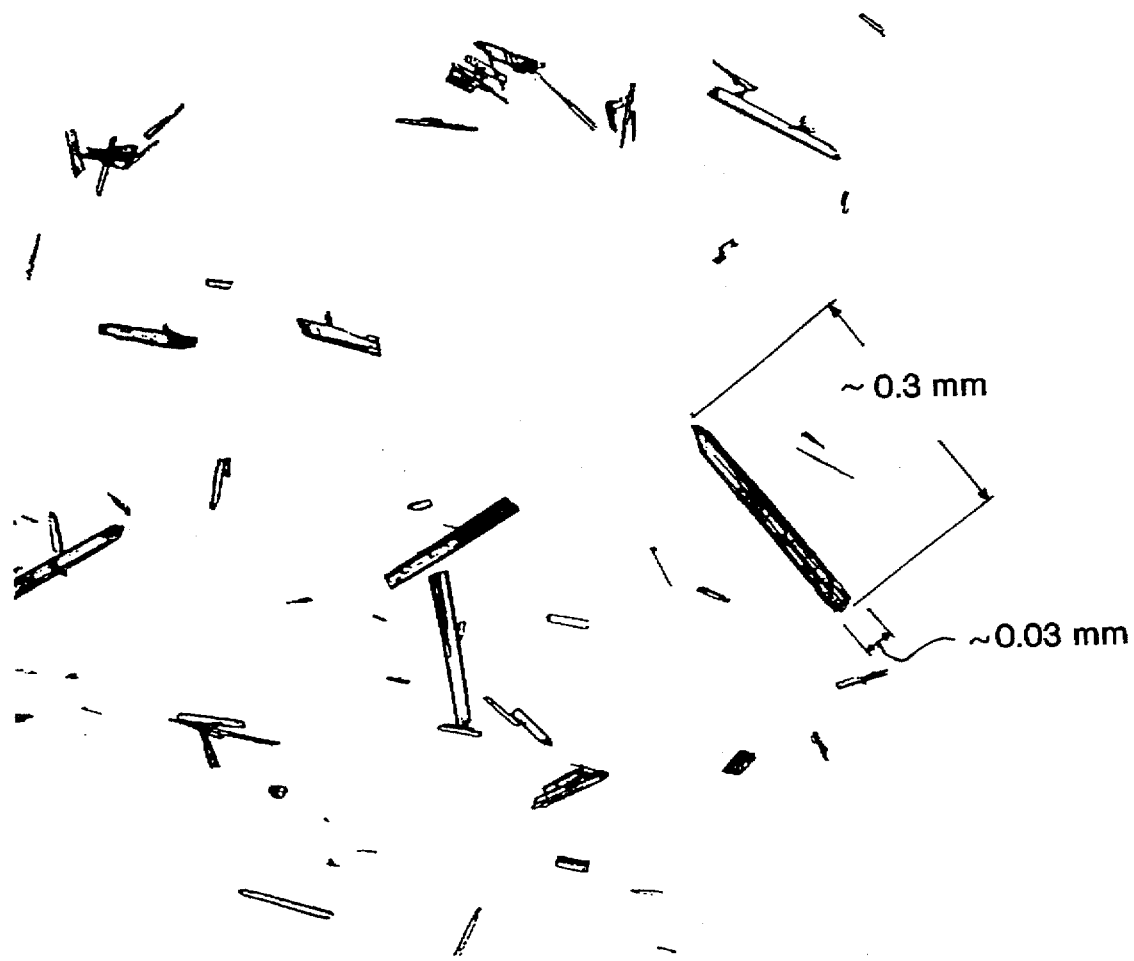

By incubation is meant all different types of crystallization processes known for a person skilled in the art.

In laboratory scale the hanging drop method is preferred, but in an industrial scale the easiest way is by letting the solution stand. The compound is preferably chosen among benzyl alcohol, 2-methylbenzyl alcohol, 1-(1-naphthyl) ethanol, phenylethanol, 1-phenyl-1-propanol, 2-phenyl-2-propanol, and 3-phenyl-1-propanol.

The invention is also related to the use of a chemical compound with the general formula (I) for the preparation of crystals of GH from a buffered solution.

When benzyl alcohol is used the preferred amount is at least 1%. The buffer could e.g. be citrate in a concentration of 2 to 50 mM, preferably 5 to 20 mM and especially 5 mM or 10 mM. The buffer can also be a mixture of sodium citrate and sodium phosphates. The aqueous solution could comprise glycine, lysine, mannitol, and/or glycerol.

An initial pH of 5.8 to 6.3 and preferably 6.2 has given good results. The formation of crystals is depending on time, pH and temperature. At a temperature of between 20° C. and 30° C. the crystals are normally rapidly formed, sometimes instantly and mostly within an hour.

Also disclosed are crystals of growth hormone or any functional analogue thereof in the form of needles, trigonal forms, cubes or parallelepipeds with a length of at least 20 micron. In some cases the obtained crystals were even more than 1 mm. Preferably the length is at least 50 to 2000 micron and more preferably 100 to 300 micron. The disclosed crystals are thus bigger than the crystals earlier obtained.

The disclosed crystals can be useful in human and veterinary usage for various administration form, e.g. topical, nasal, pulmonal, oral, rectal and parenteral.

Suspensions for injection, depot formulation and dry formulation comprising crystals according to the invention are also disclosed.

The invention is also related to a method for treating a patient in need of growth hormone or any functional analogue thereof by administering the disclosed formulation as well as for use of GH crystals for the manufacturing of a medicament for treating a patient in need of growth hormone or any functional analogue thereof.

The disclosed process can be used in a purification process for GH.

The disclosed crystals have been shown to be biologically active.

Growth hormone can be both human i.e., human growth hormone (hGH) and animal such as bovine growth hormone (bGH), fish and porcine growth hormone (pGH).

By growth hormone (GH) is meant both naturally occurring and recombinant GH (rGH). By functional analogues are meant compounds having the same therapeutic effect as the growth hormone in the animal. Preferred is the recombinant hGH. (rhGH)

By using crystals of GH the formulation is not dependent on its solubility in the used carried buffer which gives a limitation to the amount of GH per volume. This is a clear advantage of the disclosed crystals.

In a dry composition, a suspension or a depot formulation the amount per volume of GH in the drug delivery system could be very high.

Formed crystals are shown in the FIGURE: Microscopy of formed crystals

EXAMPLES 1–20

Material for formulation studies was the drug substance in the ordinary Genotropin® process. The eluate obtained after the purification process contains approx. 36 IU/ml.

Formulation was performed in laboratory scale by gel filtration which serves the purposes of removing salts used in the previous purification steps and adding the constituents of the final formulation. The column Sephadex G-25 (Pharmacia) was equilibrated with the formulation buffer. The chromatography was performed at +7° C.

The desired protein concentration was achieved by diluting with the formulation buffer. The solution was sterilely filtered and dispensed in glass cartridges.

The formation of needles in different solutions was followed in examples 1–20 and 22. The obtained hGH crystals were characterized.

Methods

Isolation

The crystals were centrifuged and the supernatant was taken away with a pipette. The residue was washed and centrifuged 6 times with water, thereafter 3 times with acetonitrile and finally twice with diethylether. The crystals were dried.

Polypeptides Size Distribution (SDS-PAGE)

Proteins in preparations of somatropin, hGH, were denatured by sodium dodecyl sulphate (SDS) to yield negatively charged molecular complexes of SDS-protein. Separation was then obtained according to molecular size by electrophoresis in polyacrylamide gels (PAGE) in the presence of SDS. The relative polypeptide size distribution of hGH was quantified by densitometric scanning of the silver stained polypeptide bands.

Thin Layer Chromatography (TLC)

Thin layer chromatography was performed on silica gel plates (Merck wt 5715) and developed in n-butanol:acetic acid:water:ethylacetate, 1:1:1:1.

Evaluation was based on three different visualization techniques, comprising UV-light at 254 nm for general screening, ninhydrin reaction for primary amino groups and potassium permanganate reagents.

ELISA, Immunosorbent Essay

Microtiter plates (Nunc a/s, Denmark) coated with immunosorbent purified rabbit antibodies directed against hGH were incubated with serum samples, references (standards) and control. After washing, Fab'anti-hGH-biotin conjugate is added and allowed to bind to the solid phase antigens. Following a further washing step, a Streptavidin-HRP conjugate is added and allowed to bind to the solid phase biotin. The amount of HRP on the solid phase is then determined using the substrates $H_2O_2$ and 3,3', 5, 5',-tetramethylbenzidine (TMBZ) and perborate. The final oxidized product is measured by its absorbance at 450 nm. The minimum detectable concentration is 0.4 mU/L. At 0.72 mU/L the intra-assay and inter-assay coefficients of variation are 2.3 and 9.0% respectively, and at 4.07 mU/L the variations are 2.2 and 11%, respectively.

HPLC

AshaiPac-OD 550, reversed phase/TRIS (pH 8.5)—n-propanol, isocratic.

Detection: 210 and 280 nm.

Gel Filtration

Superdex 75/0.05M phosphate buffer pH 7.4.

Detection: 280 nm.

Visual Inspection

The appearance of the solutions were eye-inspected according to Ph. Eur. 2nd Ed.

pH pH was measured with glass and calomel electrodes.

| Examples | 1 | 2 | 3 | 4 | 5 | 6 | 7 | 8 | 9 | 10 |
|---|---|---|---|---|---|---|---|---|---|---|
| hGH IU/ml | 20 | 20 | 20 | 20 | 20 | 20 | 20 | 20 | 20 | 20 |
| Na – citrate, mM | 10 | 10 | 10 | 10 | — | 5 | 10 | 10 | 10 | — |
| citr + phos* | — | — | — | x | — | — | — | — | — | x |
| glycine, mM | 12 | — | 12 | — | — | 12 | 12 | — | — | 12 |
| lysine, mM | — | — | — | — | — | — | — | — | — | — |
| mannitol, mM | 150 | 150 | — | — | — | 130 | 150 | 150 | — | 150 |
| glycerol | — | — | 150 | 150 | 130 | — | — | — | 150 | — |
| benzyl alc. % | 1 | 1 | 1 | 1 | 1.25 | 1 | 1 | 1 | 1 | 1 |
| Volume, ml | 1 | 1 | 1 | 1 | 1 | 3.4 | 1 | 1 | 1 | 1 |
| Starting values: | | | | | | | | | | |
| pH | 6.3 | 6.3 | 6.2 | 6.2 | 6.1 | 6.2–6.3 | 6.2 | 6.2 | 6.2 | 6.2 |
| visual inspect. | clear | clear | clear | clear | clear | clear | clear | clear | clear | clear |
| The results after 3 weeks' storage at 30° C.: | | | | | | | | | | |
| pH | 6.3 | 6.3 | — | — | — | 6.2 | 6.3 | 6.3 | 6.3 | 6.4 |
| visual inspect. | clear | clear | cryst | cryst | cryst | cryst | cryst | cryst | cryst | cryst |

| Examples | 11 | 12 | 13 | 14 | 15 | 16 | 17 | 18 | 19 | 20 |
|---|---|---|---|---|---|---|---|---|---|---|
| hGH IU/ml | 20 | 20 | 20 | 20 | 20 | 20 | 20 | 4 | 20 | 20 |
| Na – citrate, mM | — | — | — | 10 | 10 | 10 | — | 10 | 5 | — |
| citr + phos* | x | x | x | — | — | — | x | — | — | x |
| glycine, mM | — | 12 | — | — | 29 | — | 12 | 12 | 12 | 12 |
| lysine, mM | — | — | — | 12 | — | 29 | — | — | — | — |
| mannitol, mM | 150 | — | — | 130 | 130 | 130 | 250 | 250 | 250 | 250 |
| glycerol | — | 150 | 150 | — | — | — | — | — | — | — |
| benzyl alc. % | 1 | 1 | 1 | 1.5 | 1.5 | 1.5 | — | — | — | — |
| Volume, ml | 1 | 1 | 1 | 1 | 1 | 1 | 1 | 3 | 1 | 1 |
| Starting values: | | | | | | | | | | |
| pH | 6.2 | 6.2 | 6.2 | 6.2 | 6.2 | 6.1 | 6.3 | 6.3 | 6.1 | 6.3 |
| visual inspect. | clear | clear | clear | op** | op** | op** | clear | clear | clear | clear |
| The results after 3 weeks' storage at 30° C.: | | | | | | | | | | |
| pH | 6.3 | 6.3 | 6.3 | | | | 6.4 | 6.2 | 6.2 | 6.4 |
| visual inspect. | cryst | cryst | cryst | | | | clear | clear | clear | clear |
| The result after 3 months' storage at 5° C. | | | | | | | | | | |
| pH | | | | 6.3 | 6.3 | 6.3 | | | 6.3 | 6.3 |
| visual inspect. | | | | cryst | cryst | cryst | | | clear | clear |

*x means a mixture of 1.7 mM Na citrate and 6.7 mM Na phosphate buffer system.
**means opalescent

Discussion

Normally our formulations comprising benzyl alcohol gave crystals in the pH range of 6.1 to 6.3 and the solutions without benzylalcohol gave no crystals within this pH range. Formulations 1 and 2 were clear in spite of the addition of benzyl alcohol at pH 6.3 which appears to be a critical value for the formation of crystals in benzyl alcohol.

Results and Identification

Microscopy

The crystals were in the form of needles of different length. The biggest were about 0.3×0.03 mm. See FIG. 1.

Melting Point Determination

The melting point was performed on a Leitz-Wetzlar microscope. No melting point could be observed. The crystals were intact up to 230° C., when they started to be miscoloured. At about 290° C. the crystals were black but not melted. (pyrolysis)

Solubility

The crystals were insoluble in organic solvents such as dichloromethane, acetonitrile, ethanol, dimethyl formamide, and diethylether. They were difficult to dissolve in water and 70% ethanol in water but soluble in acids such as 1% acetic acid, 6M HCl and in a base such as 0.1M phosphate buffer, pH 8.

Thin Layer Chromatography (TLC)

The crystals, dissolved in 10% acetic acid and the buffer components, i.e. citric acid, mannitol, glycine and benzylic alcohol were investigated.

The crystal sample did not migrate in this system, whereas all buffer components did.

The crystal sample absorbed UV-light and showed positive reaction with ninhydrin and permanganate reagents, indicating the presence of aromatic groups, amino groups and oxidizable groups.

Hydrolysis

Hydrolysis in 6M HCl, 110° C., 20 hours of the crystal sample and hGH reference. Analysis by using TLC showed identical spots.

HPLC, Gel Filtration, SDS-Page, IEF

The crystal sample was almost identical with the hGH reference.

Amino Acid Analysis

Experimental data obtained on the crystals was in good agreement with the theoretical value as well as with the hGH reference sample. See table below:

| Component | Theoretical value | crystals |
| --- | --- | --- |
| Asp | 20 | 19.9 |
| Thr | 10 | 9.7 |
| Ser | 18 | 17.8 |
| Glu | 27 | 26.8 |
| Pro | 8 | 8.2 |
| Gly | 8 | 8.2 |
| Ala | 7 | 7.0 |
| Half-cys | 4 | 3.2 |
| Val | 7 | 7.2 |
| Met | 3 | 3.0 |
| Ile | 8 | 8.2 |
| Leu | 26 | 26.2 |
| Tyr | 8 | 8.2 |
| Phe | 13 | 13.0 |
| His | 3 | 3.1 |
| Lys | 9 | 9.3 |
| Trp | 1 | * |
| Arg | 11 | 11.1 |

* Not determined

The protein content of the crystal sample, based on an amount of 0.22 mg, was 84%. The content in the reference material (0.45 mg) was 91%.

EXAMPLE 21

No crystals were formed in a solution containing:

20 IU/ml hGH 5 mM Na-citrate, 12 mM glycine 250 mM mannitol and

1% benzyl alcohol at a pH of 6.4.

With the addition of more benzyl alcohol (i.e. >1%) the crystals were however rapidly formed.

Crystals were also produced by lowering pH closer to 6 or under 6.

The morphology of the crystals could be varied by pH and growth rate. When pH is closer to 6.3 the crystals are like needles and parallelepipeds.

Within 24 hours crystals are formed with a length of 0.1 to 0.3 mm and about 0.001 to 0.005 mm thick.

By varying the pH the size of the crystals could thus be changed.

Smaller crystals are formed within a shorter time.

EXAMPLE 22

Other chemical compounds were investigated for the possibility of forming crystals of growth hormone.

Material for formulation studies was the drug substance in the ordinary Genotropin® process. The eluate obtained after the purification process contains approx. 36 IU/ml before formulation.

Formulation was performed in laboratory scale by dialysis against the used buffer.

The method "hanging drop" was used for investigation of useful agents for crystallization of growth hormone. The "hanging drop" method is described in Crystallisation of Nucleic Acids and Proteins, A practical approach, by A Ducruix and R Giegé, IRL Press at Oxford, 1991, pages 82–86.

The initial volume of the drop was 5 µl+5 µl and the well volume 1 ml. The buffer used during the experiments comprised the following ingredients:

Compound as given below 200 mM Na-citrate pH 6.2

The results were the following with the different crystallisations agents:

| Compound | Crystals |
| --- | --- |
| benzyl alcohol | large single |
| ±1-(1-naphthyl)ethanol | large single |
| (±)phenylethanol | large single |

| Compound | Crystals |
| --- | --- |
| +phenylethanol | large single |
| −phenylethanol | large single |
| 1-phenyl-1-propanol | large single |
| (±)1-phenyl-propanol | large single |
| 2-phenyl-2-propanol | large single |
| 3-phenyl-1-propanol | large single |
| 2-methylbenzyl alcohol | single |

For some of the used crystallization agents the crystals were formed slower. When using ±1-(1-naphthyl)ethanol the crystals were formed after a couple of weeks, and the size was 200 to 500 microns. Instead of using Na-citrate, also MES-buffer was used. The results were the same as when using Na-citrate.

A higher concentration of the crystallization agent was, however, needed when no citrate was present.

When other crystallization agents were tested in the same way as above, falling outside the general formula (I), no crystals were formed:

| Compound | Crystals |
| --- | --- |
| 3-methyl-4-nitrobenzyl alcohol | none |
| 2-nitrobenzyl alcohol | none |
| 4-nitrobenzyl alcohol | none |
| 1-naphthol | none |
| 2-naphthol | none |
| phenol | none |
| benzaldehyde | none |
| benzylamine | none |
| (−)1-phenyl-1-butanol | none |
| L-phenylglycinol | none |

EXAMPLE 23

Immunological analysis of the crystals was performed. The crystals were formed according to examples 1–20 in a buffer containing:

20 IU/ml growth hormone 5 mmol Na-citrate 12 mmol glycine 130 mmol mannitol

1% benzyl alcohol.

0.17 mg of the formed crystals were dissolved in 0.340 ml 0.05M phosphate buffered saline, pH 7.5 containing 0.05% Tween 20. The solution was further diluted in 10 fold steps in the same buffer. All individual dilution steps were analysed in quadruplicates.

An enzyme-linked immunosorbent assay, ELISA, Immunosorbent assay, was used to measure rhGH in the dissolved crystals.

The amount of rhGH in the vial was found to be 0.15 mg.

EXAMPLE 24

Bioassay

Crystals have been grown from a solution according to example 6 above and dispensed as 0.5 ml samples in glass containers. After preparation the solution was stored at 25° C. for 1 week for the crystals to grow. They were stored further at 5° C. for 3 months prior to crystal harvesting. When the crystals were harvested the supernatant surrounding the crystals was sucked of. The crystals were rinsed twice with 0.25 ml of buffer according to example 6 (i.e. the composition according to example 6 except for the growth hormone). The second rinsing step was terminated by centrifugation of the crystals prior to discarding the rinsing buffer. The remaining crystals were dissolved in 0.5 ml of buffer of 5 mM sodium citrate, 12 mM glycine and 130 mM mannitol, pH 6.1. Several samples were pooled to be used in the bioassay analysis.

Gel filtration chromatography was run on a sample prepared according to the above procedure. The growth hormone showed to be 100% monomeric after crystallization and subsequent dissolution.

Bioassay of Dissolved Growth Hormone (GH) Crystals

To investigate whether the GH crystals obtained were biologically active, a weight gain assay in hypophysectomized rats was performed.

Rats were purchased from Möllegaard A/S, Denmark. The rats were hypophysectomized the week before arrival and therefore lacking endogenous growth hormone and other pituitary hormones, resulting in stunted growth. The rats were weighed at arrival in the lab and before assay. Rats changing weight <10% were accepted to enter the study.

The rats were then divided randomly into groups of 15. They were treated twice daily for 4 days with either an in-house standard preparation of human recombinant GH (calibrated against WHO 80/505 to have a biological potency of 4.5 IU/vial) or the solution made from GH crystal at two doses. Standard doses were 0.04 IU/day and 0.16 IU/ml.

The groups were weighed before the first injection (day 1) and approximately 16 hours after the last injection (day 5) The difference between these weights were calculated and the potency determined by comparing the results of the crystal solution treated animals with those of the standard treated groups.

The results are shown below (weight gain, g SD):

| Dose | 0.04 IU/day | | 0.16 IU/day | |
| --- | --- | --- | --- | --- |
| Standard | 12.2 | 8.9 | 17.7 | 8.7 |
| GH crystals | 17.3 | 8.0 | 21.3 | 1.7 |

The biological potency of the dissolved GH crystals was found to be 7.1 IU/ml.

Thus, we have demonstrated that the human growth hormone in dissolved GH crystals is biologically active in vivo.

We claim:

1. Process for manufacturing crystals of human growth hormone (GH) in the form of needles, trigonal forms, cubes or parallelepipeds with a length of at least 20 microns, which comprises the following steps:

i) mixing human GH with an aqueous solution consisting essentially of a buffer and a chemical compound with the general formula (1):

$$Ar-(-CR_1R_2-)_n-(-CR_3R_4-)_m-CR_5R_6-OH \quad (1)$$

in which

Ar is phenyl, alkyl-substituted phenyl, naphthyl, or alkyl-substituted naphthyl $R_1$ to $R_6$ is H, OH or alkyl n and m is 0 or 1, and in the absence of added cations and in the absence of solvents selected from the group consisting of methanol, ethanol and paraldehyde;

ii) incubating; and iii) isolating said crystals with a length of at least 20 microns; and wherein said solution has an initial pH of 5.8 to 6.3 and the concentration of said buffer is about 2 to about 50 mM.

2. Process according to claim 1, in which GH is recombinant human GH (rhGH).

3. The process according to claim 1 wherein said compound is selected from the group consisting of benzyl alcohol, 2-methylbenzyl alcohol, 1-(1-naphthyl)ethanol, phenylethanol, 1-phenyl-1-propanol, 2-phenyl-2-propanol, and 3-phenyl-1-propanol.

4. Process according to claim 3 in which the compound is benzyl alcohol.

5. Process according to claim 4 in which the amount of benzyl alcohol is at least 1%.

6. Process according to claim 2 in which the compound is selected from the group consisting of benzylalcohol, 2-methylbenzylacohol, 1-(1-naphthyl)ethanol, phenylethanol, 1-phenyl-1-propanol, 2-phenyl-2-propanol, and 3-phenyl-1-propanol.

7. The process of claim 1 wherein the length of said crystals is 50 to 2000 microns.

8. The process of claim 1 wherein the length of said crystals is 100 to 300 microns.

9. The process of claim 1 wherein said buffer includes a citrate.

10. The process of claim 9 wherein said citrate is present in a concentration of 2 to 50 mM.

11. The process of claim 9 wherein said citrate is present in a concentration of 5 to 20 mM.

12. The process of claim 9 wherein said citrate is present in a concentration of 5 mM or 10 mM.

13. The process of claim 1 wherein said buffer is a mixture of sodium citrate and sodium phosphate.

14. The process of claim 1 wherein said aqueous solution further includes at least one member selected from the group consisting of glycine, lysine, mannitol, glycerol and mixtures thereof.

15. The process of claim 1 wherein said pH is 6.2.

16. The process of claim 1 wherein said pH is 6.3.

17. The process of claim 1 wherein said incubating is carried out at temperatures of between 20° C. and 30° C.

18. The process of claim 17 wherein said crystals are formed within one hour.

19. The process of claim 1, wherein said compound is present in an amount of at least 1%; said incubating is carried out at temperatures of between 20° C. and 30° C., and said crystals are formed within one hour.

20. The process of claim 19 wherein said buffers includes a citrate and said compound is selected from the group consisting of benzyl alcohol, 2-methylbenzyl alcohol, 1-(1-naphthyl)ethanol, phenylethanol, 1-phenyl-1-propanol, 2-phenyl-2-propanol, 3-phenyl-1-propanol.

21. The process of claim 19 wherein said compound is benzyl alcohol.

22. The process of claim 21 wherein said buffer is a mixture of sodium citrate and sodium phosphate.

23. The process of claim 21 wherein said aqueous solution further includes at least one member selected from the group consisting of glycine, lysine, mannitol, glycerol and mixtures thereof.

24. Process according to claim 19, in which GH is recombinant human GH (rhSH).

* * * * *

UNITED STATES PATENT AND TRADEMARK OFFICE
CERTIFICATE OF CORRECTION

PATENT NO. : 5,734,026
DATED : March 31, 1998
INVENTOR(S): Florin-Robertsson et al It is certified that error appears in the above-identified patent and that said Letters Patent is hereby corrected as shown below:

```
Title page, [75] Inventors: should read --Ebba-Florin-
Robertsson, Stockholm; Elvy Hökby, Enskede; Ronny Lundin,
Ekerö; Sirkka Thomé, Stockholm; Gertrud Westin-Sjödahl,
Södertälje, Tomas Lundqvist, Stockholm, all of Sweden--.
```

Signed and Sealed this

Twenty-eighth Day of July, 1998

Attest:

BRUCE LEHMAN

*Attesting Officer*     *Commissioner of Patents and Trademarks*